United States Patent
Gebauer

(10) Patent No.: US 10,099,047 B2
(45) Date of Patent: Oct. 16, 2018

(54) ASEPTIC CONNECTION OF SEPARATION OR REACTION SYSTEMS

(75) Inventor: Klaus Gebauer, Uppsala (SE)

(73) Assignee: GE Healthcare Bio-Sciences AB, Uppsala (SE)

(*) Notice: Subject to any disclaimer, the term of this patent is extended or adjusted under 35 U.S.C. 154(b) by 0 days.

(21) Appl. No.: 13/521,242

(22) PCT Filed: Jan. 10, 2011

(86) PCT No.: PCT/SE2011/050010
§ 371 (c)(1),
(2), (4) Date: Jul. 10, 2012

(87) PCT Pub. No.: WO2011/084101
PCT Pub. Date: Jul. 14, 2011

(65) Prior Publication Data
US 2013/0048111 A1    Feb. 28, 2013

(30) Foreign Application Priority Data
Jan. 11, 2010  (SE) ........................ 1050007

(51) Int. Cl.
*B01D 15/08*    (2006.01)
*B01D 35/30*    (2006.01)
(Continued)

(52) U.S. Cl.
CPC ........... *A61M 39/162* (2013.01); *A61M 39/16* (2013.01); *A61M 39/165* (2013.01); *A61M 39/18* (2013.01);
(Continued)

(58) Field of Classification Search
CPC ........... A61M 1/68; A61M 2001/1633; A61M 2001/168; B01D 15/08; B01D 25/002;
(Continued)

(56) References Cited

U.S. PATENT DOCUMENTS

| | | | | |
|---|---|---|---|---|
| 3,865,411 | A | * | 2/1975 | Rowe et al. .................. 285/363 |
| 5,470,487 | A | | 11/1995 | Staats, III et al. |
| 6,149,699 | A | | 11/2000 | Grantham |
| 6,679,529 | B2 | * | 1/2004 | Johnson ................ A61M 39/18 285/3 |
| 2002/0008063 | A1 | * | 1/2002 | Zuk, Jr. ............... A61M 1/3633 210/435 |
| 2002/0014106 | A1 | | 2/2002 | Srinivasan et al. |
| 2003/0030272 | A1 | | 2/2003 | Johnson et al. |
| 2003/0066794 | A1 | | 4/2003 | Diel |
| 2004/0155211 | A1 | | 8/2004 | Takeda et al. |
| 2005/0279694 | A1 | | 12/2005 | Straeffer et al. |

(Continued)

FOREIGN PATENT DOCUMENTS

| | | |
|---|---|---|
| CN | 1232240 C | 12/2005 |
| CN | 1721033 | 1/2006 |

(Continued)

OTHER PUBLICATIONS

Search Report dated Feb. 7, 2014 Issued on Corresponding Chinese Patent Application No. 201180005717.X.

*Primary Examiner* — Claire A Norris
(74) *Attorney, Agent, or Firm* — Wood IP LLC

(57) ABSTRACT

A separation or reaction unit (1; 1'; 81; 81'; 101) and a method for aseptically connecting such units. The separation or reaction unit (1; 1'; 81; 81'; 101) comprises at last one fluid inlet (3a, 3b, 5a, 5b; 3a', 3b', 5a', 5b'; 85a, 85b; 103a, 103b) and at least one fluid outlet (3a, 3b, 5a, 5b; 3a', 3b', 5a', 5b'; 85a, 85b; 103a, 103b). At least one of the inlet or outlet is sealed by at least one film (7, 9; 11; 87a, 87b; 107a, 107b) and the contact surface between the film and the separation or reaction unit is aseptic. The films are adapted to be mated with a corresponding film on another separation or reaction unit or on a fluid distribution unit (20; 57; 61) which the separation or reaction unit possibly should be connected with and said mated films are adapted to be pulled out together two and two after mating such that corresponding fluid inlets/outlets on the two connected units are mated aseptically.

7 Claims, 7 Drawing Sheets

(51) Int. Cl.
  *B01D 25/00* (2006.01)
  *A61M 39/16* (2006.01)
  *A61M 39/18* (2006.01)
  *G01N 30/96* (2006.01)
  *G01N 30/88* (2006.01)

(52) U.S. Cl.
  CPC ..... *G01N 30/96* (2013.01); *G01N 2030/8881* (2013.01); *Y10T 137/0402* (2015.04); *Y10T 137/794* (2015.04)

(58) Field of Classification Search
  CPC ...... B01D 25/02; B01D 27/14; B01D 27/146; B01D 2201/305; B01D 2201/308; B01D 2201/4038; B65D 55/06; B65D 55/0818; B65D 55/0827; B65D 2101/0023; B65D 2517/0013; B65D 2517/0017; F16J 15/06; C02F 1/44; C02F 2201/004
  USPC ......... 210/259, 198.2, 232, 252, 264, 323.1, 210/355; 422/70, 139, 141, 142, 600, 422/608, 630; 277/590
  See application file for complete search history.

(56) References Cited

U.S. PATENT DOCUMENTS

2005/0279695 A1\* 12/2005 Straeffer ................ B01D 25/26 210/335
2007/0241048 A1\* 10/2007 Hunt et al. .................... 210/450

FOREIGN PATENT DOCUMENTS

| | | |
|---|---|---|
| CN | 200945309 Y | 9/2007 |
| EP | 1967244 | 9/2008 |
| JP | 55-095804 U1 | 3/1980 |
| JP | 63-153261 U1 | 10/1988 |
| JP | 2000-093816 | 4/2000 |
| JP | 2000-227714 | 8/2000 |
| JP | 2001-249528 | 9/2001 |
| JP | 2003-241494 | 8/2003 |
| JP | 2007-162899 | 6/2007 |

\* cited by examiner

ASEPTIC CONNECTION OF SEPARATION OR REACTION SYSTEMS

CROSS-REFERENCE TO RELATED APPLICATIONS

This application is a filing under 35 U.S.C. 371 of international application number PCT/SE2011/050010, filed Jan. 10, 2011, published on Jul. 14, 2011 as WO 2011/084101, which claims priority to application number 1050007-2 filed in Sweden on Jan. 11, 2010.

TECHNICAL FIELD OF THE INVENTION

The present invention relates to a separation or reaction unit, a fluid distribution unit, a separation or reaction system and to a method for providing aseptic connections between at least two separation or reaction units or at least one separation or reaction unit and at least one fluid distribution unit.

BACKGROUND OF THE INVENTION

Single use systems, also called disposable systems are more and more used in the bioprocess industry. For example separation or reaction systems such as chromatography systems, filter systems or bioreactor systems have today at least partly been provided as disposable systems. This eliminates the need for cleaning and cleaning validation before processing, in between processes and cycles or after processing before re-use as required for conventional re-usable equipment. With disposable systems cross-contamination is avoided.

Bioburden control of single-use equipment during manufacturing of the equipment itself is required to eliminate cleaning needs before bringing single-use equipment into product contact. This is usually achieved by manufacturing of single-use equipment in controlled environment (clean room), often followed by sterilisation processes (gamma irradiation). The demands of the level of bioburden control can differ for different applications, however, bioburden control to a certain degree of the equipment is not only required for some applications, but also considered as the preferable for most of the applications using disposable equipment. The production of this equipment in controlled environments is required to guarantee a low initial level of contaminants prior to the bioburden control procedure, hereby reducing for example endotoxin levels. Sterility and asepsis are terms used to define the state of a system, a piece of equipment or a fluid conduit as being in control of bioburden levels to different degrees.

Aseptic connectors can be used to interconnect single-use equipment and also single-use equipment and conventional re-use equipment that is bioburden controlled (santized, sterilised etc.). Available aseptic connectors are for example ReadyMate connectors from GE Healthcare and Kleenpack from Pall.

Typical applications of aseptic connectors in biomanufacturing are connections between fluid lines, separation units (filters, chromatography columns, adsorbers, membrane adsorbers, expanded or fluidized bed adsorbers) or reaction units (bioreactors, reaction or (bio-)conversion units that for example utilize enzymatic conversions).

An example of a disposable separation system built up from a number of units is described in US20070241048. A problem with this system is that in order to maintain asepsis (or bioburden control) at process side when assembling the unit, assembly has to be done in a controlled environement (LAF bench).

A possible solution with today available technique is to connect each separate disposable separation or reaction unit with aseptic connectors. However this is not cost efficient and separation efficiency is reduced due to high hold-up volume in interconnecting fluid lines.

Hereby, disposable separation or reaction systems available today are not flexible when it comes to the capacity of the system.

SUMMARY

One object of the invention is to provide a more flexible separation or reaction system.

This is achieved by a method according to claim 18. Hereby a number of different separation or reaction units can be combined in an aseptic way. Hereby the customer can by himself design the separation or reaction system and provide an aseptic separation or reaction system with a wanted capacity.

This is also achieved by a separation or reaction system according to claim 16 and by a separation or reaction unit according to claim 1, and possibly also by a fluid distribution unit according to claim 10.

Suitable embodiments are described in the description and in the dependent claims.

DETAILED DESCRIPTION OF THE EMBODIMENTS

Figure 1A:
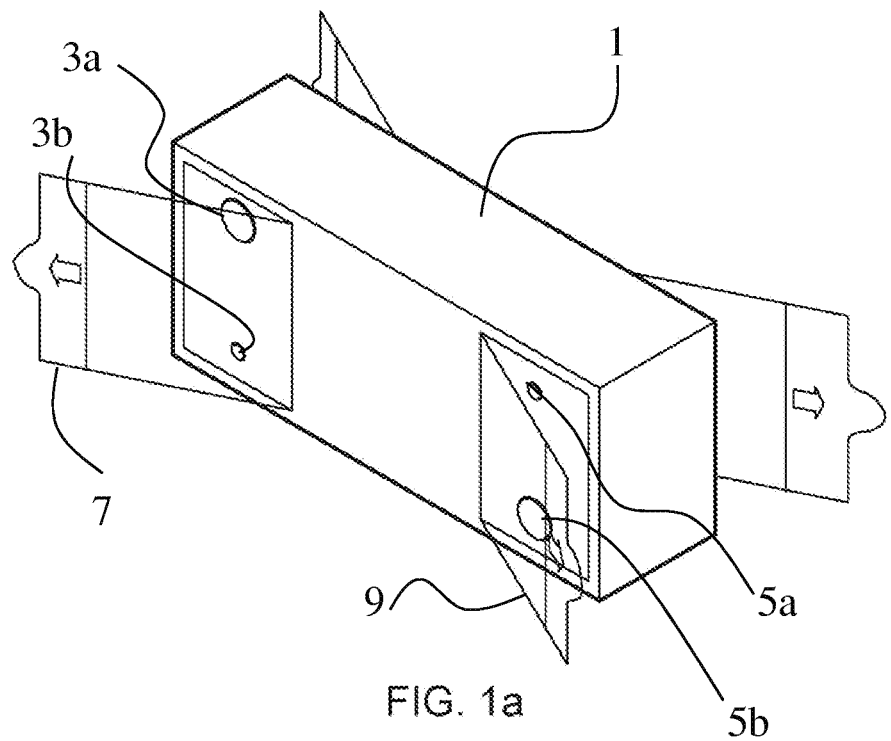
FIG. 1a shows a separation unit according to one embodiment of the invention.

The word aseptic used in this description and in the claims shall have a broad definition, i.e. include any level of bioburden control. The bioburden control or asepsis can be measured as organisms/ml or CFU (colony forming units). In one embodiment of the invention the level of asepsis should be below 100 CFU/ml. The latter corresponds to bioburden control levels required for food grade products. Low levels of bioburden can be achieved by sterilisation processes. For example the units of the invention can be subjected to gamma sterilization. Other possible methods are autoclaving or bioburden control by ethylene dioxide.

The present invention relates to aseptic separation or reaction units that can be connected in an aseptic way. Suitably the units are disposable. The separation or reaction units can for example be filter cassettes to be provided in a filter system, chromatography units to be provided in a chromatography system or reaction units. The group of filter systems shall include at least Normal Flow Filters such as aseptic filters, particle removal filters or virus removal filters and Cross-flow filters. The group of chromatography units shall include packed bed chromatography, monoliths or other types of fixed beds but also modified membranes (membrane adsorbers) and other types of surfaces or structures that are employed for achieving a separation by means of a sorption process. The nature of the sorption process can be based on ion exchange, bio-affinity, hydrophobicity etc. and is suitably performed as a liquid based adsorption process. The group of reaction units shall include fixed bed reactors, for example for bioconversion processes, but also other configurations that rely on reactions that are at least partly run in free solution or a fluid.

With this invention any desired number of separation or reaction units can be connected to each other in a system in an aseptic way. Hereby an aseptic system, for example a filter system or chromatography system, of any desired capacity can be built from units. Furthermore, these systems can be built in an environment that is not bioburden controlled and the system with all its connections will still be aseptic on process side. According to the invention a protection film is provided over the inlets/outlets of the separation or reaction units. The film is suitably provided to the units before the unit is subjected to sterilisation. This means that the separation or reaction unit with the attached film can be treated in a non sterile environment while the contents of the unit confined by its inlets/outlets including the inlets/outlets still are kept sterile or aseptic. The film is folded over the inlets/outlets and one single sheet of the film is reaching outside the unit. The film should be mated with a similar film on a connecting unit and the two films should be released together by pulling the two single sheets reaching outside the units when the units are pressed together. This ensures that the inlets/outlets on the two units will be connected in an aseptic way. Furthermore, to enable a fluid tight connection between the units at least one gasket is provided around each inlet/outlet or around a number of inlets/outlet if suitable for the device and application. A foam layer is provided around the gaskets such that the units can be pressed together to a first aseptic connection position where the protective films can be removed without exposing the aseptic process side to the environment, which may be non-sterile. The purpose of the compressible foam pads is to provide the required degree of volumetric variability to allow for an expansion of the two opposite foam pads against each other to remain asepsis when removing the adjacent folded films by pulling. This first connection position is suitably secured by a frame device or by a locking arrangement provided on each unit (further described below).

When the films have been released in this first connection position the units are pressed together even further to a second position. In the second position a fluid tight seal is provided through the gaskets having been engaged.

Suitably the separation or reaction units are disposable, i.e. adapted to be used only once. One advantage with disposable systems is that there is no need for cleaning and bioburden control before using the systems because disposable systems are already aseptic in some degree and they should not be used again and need therefore not be cleaned between uses. Therefore the aseptic connection method and means provided with this invention is particularly interesting in disposable systems. With the invention disposable systems, such as filter systems or chromatography systems can be built up from different units to a wanted capacity by the customer while still keeping the asepsis requirements. Below some example embodiments of the invention are given.

Figure 1B:
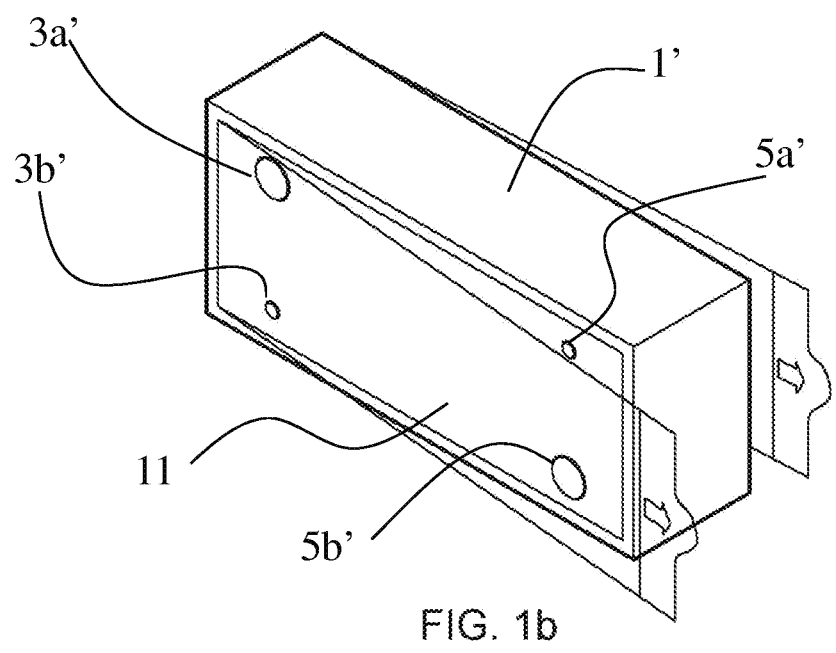
FIG. 1b shows a separation unit according to another embodiment of the invention.

FIG. 1a shows a separation unit 1 according to one embodiment of the invention. In this embodiment the separation unit is a filter cassette 1 that is aimed for running a cross-flow filtration process. In this example the filter cassette comprises two first inlets/outlets 3a, 3b on the left side (referring to the FIG. 1a) of the filter cassette 1 and two second inlets/outlets 5a, 5b on the right side of the filter cassette 1. The number of inlet/outlets can of course vary. According to the invention a first film 7 is provided on the left side of the filter cassette covering the first inlets/outlets 3. A second film 9 is provided on the right side of the cassette covering the second inlets/outlets 5a, 5b. In FIG. 1b another embodiment of a separation unit 1' according to the invention is shown. Here both first inlets/outlets 3a', 3b' on the left side of the separation unit 1' and second inlets/outlets 5a', 5b' on the right side of the separation unit 1' are covered by one single film 11. In these views only one side of the filter cassettes 1, 1' can be seen. However, the back sides of these units are suitably designed in the same way with inlets/outlets and covering films (the films can be seen pointing out from the back sides). The surface between the films 7,9,11 and the filter cassettes 1, 1' is aseptic. As described in the beginning of the description aseptic can mean different levels of bioburden control depending on the requirements.

Figure 2A:
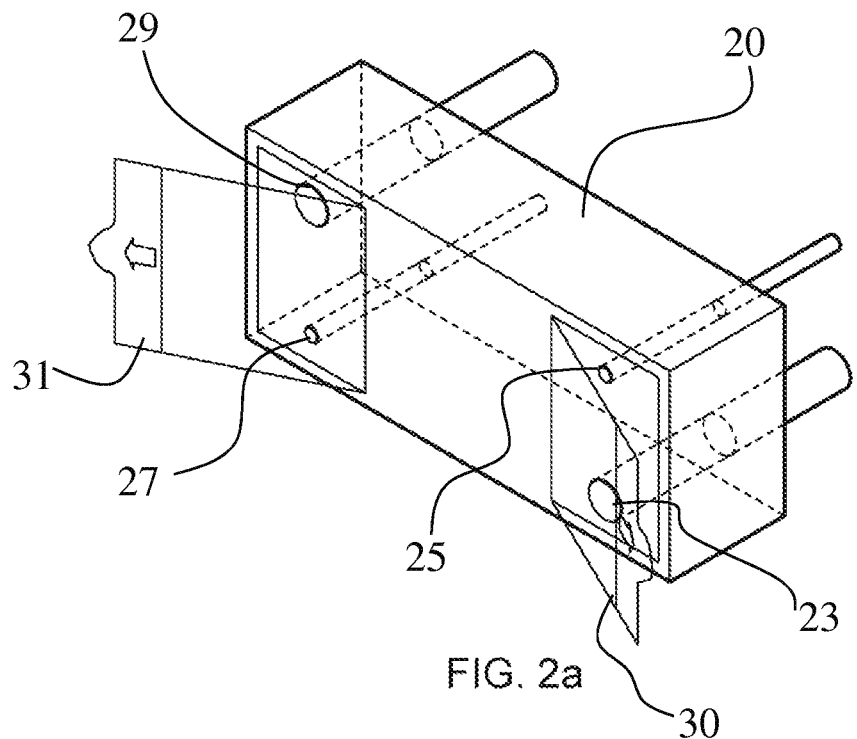
FIGS. 2a and 2b show the two sides of a fluid distribution unit to be used together with the separation unit shown in FIG. 1a in a separation system according to one embodiment of the invention.
Figure 2B:
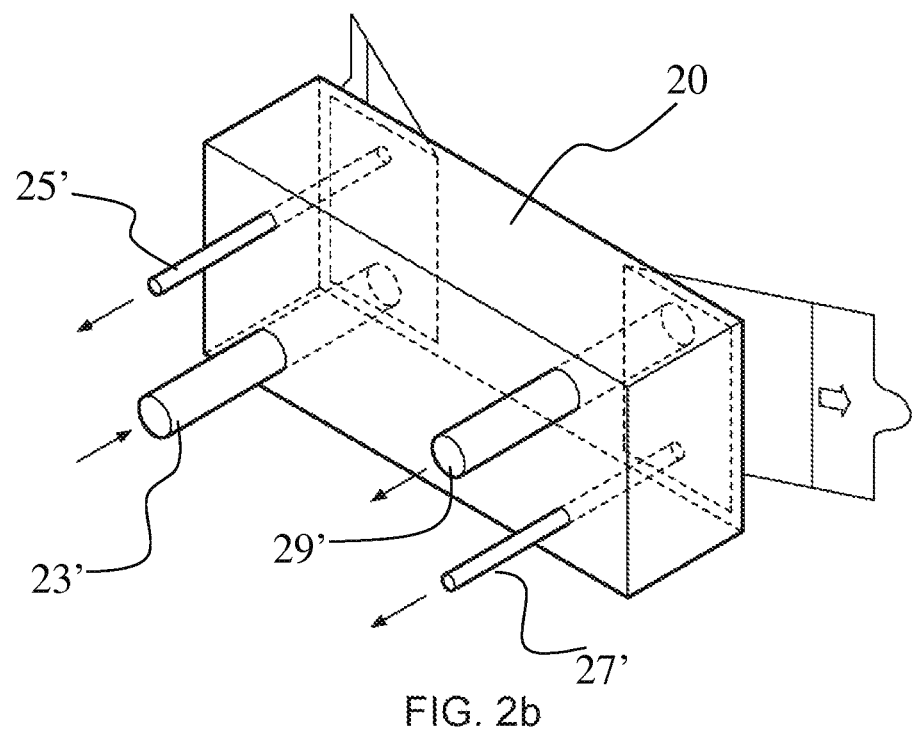

FIGS. 2a and 2b show a fluid distribution unit 20 to be used together with the separation unit 1 shown in FIG. 1a in a separation system according to one embodiment of the invention. In this embodiment the fluid distribution unit 20 is adapted to be used in a filter system and comprises on the side adapted to be connected to the filter unit (the front side in FIG. 2a) four inlet/outlets in positions that correspond with the positions of the inlet/outlets 3a,b,5a,b. In this example a distribution unit inlet 23 is provided at the lower part on the right side (reference to FIG. 2a) of the distribution unit 20 and a first distribution unit outlet 25 (permeate—retentate?) is provided above the inlet 23 and a second and a third distribution unit outlet 27, 29 are provided on the left side of the distribution unit 20. All the inlets/outlets 23, 25, 27, 29 are positioned correspondingly with the inlets/outlets 3a,b, 5,a,b of the filter unit 1 to which is adapted to connect. According to the invention the distribution unit inlets/outlets are covered by films. In this embodiment a first film 30 covers distribution unit inlet 23 and the first distribution unit outlet 25 and a second film 31 covers the second and third distribution unit outlets 27, 29. Furthermore these films 30, 31 have the same dimensions as the first and second films 7, 9 on the filter cassette to which this fluid distribution unit should be connected. As before the surface between the films and the fluid distribution unit is aseptic.

In FIG. 2b the other side of the fluid distribution unit 20 shown in FIG. 2a is shown. Here a distribution unit fluid inlet connection 23' is shown which is connected to the distribution unit inlet 23 on the other side of the fluid distribution unit 20. Furthermore a first, second and third distribution unit fluid outlet connections 25', 27', 29' are shown which all are connected to corresponding outlets on the other side of the fluid distribution unit 20.

Figure 3:
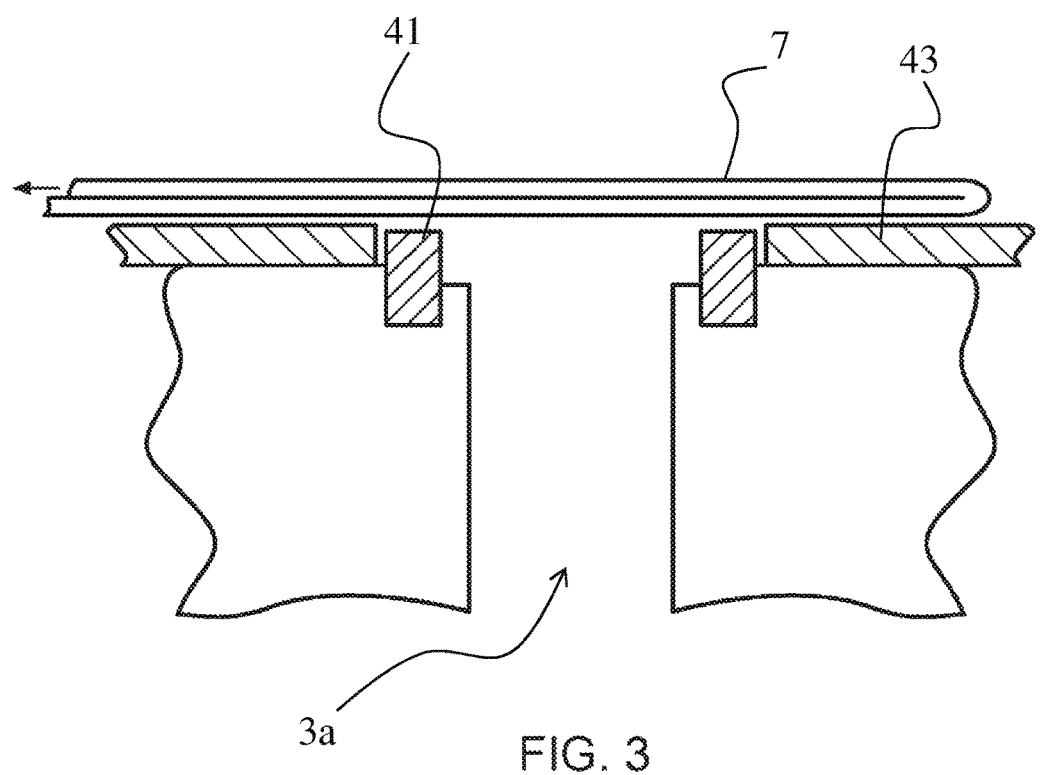
FIG. 3 shows a film and connection parts provided to for example a separation unit as shown in FIG. 1a or 1b or a fluid distribution unit as shown in FIGS. 2a and b.

FIG. 3 shows a film and connection parts provided as aseptic barrier to for example a separation unit as shown in FIG. 1a or 1b or a fluid distribution unit as shown in FIGS. 2a and b. In FIG. 3, reference numbers corresponding to the film on the right side of FIG. 1a is used. An inlet/outlet, here the first inlet/outlet 3a in FIG. 1a is illustrated in cross section. (However all the other inlets/outlets could be illustrated similarly). Around the first inlet/outlet 3a a gasket 41 is provided. One gasket can be provided around each of the inlets/outlets on both the separation/reaction units and the fluid distribution units. In some cases it would also be possible to provide one gasket around more than one inlet/outlet. Furthermore a compressive foam layer 43 is provided around the gasket 41. The folded film 7 is provided over the first inlet/outlet 3a, the gasket 41 and the foam layer 43. The connection surface between the film 7 and the gasket 41 and the foam layer 43 is as described above aseptic.

The film 7 is folded unevenly such that the film is provided double over the separation or reaction unit or fluid distribution unit and as a single sheet of the uppermost layer is reaching outside the separation, reaction or fluid distribution unit. This part is used for being grabbed and for pulling out the film together with a matching film when the system is connected. When two separation units as shown in FIG. 1 are connected the films are mated two and two together and during connection the films are supposed to be pulled out together two and two. Hereby the aseptic surfaces of the separation units (previously covered by the films) will be mated and the asepsis will be maintained. This will be described in more detail below.

Figure 4A:
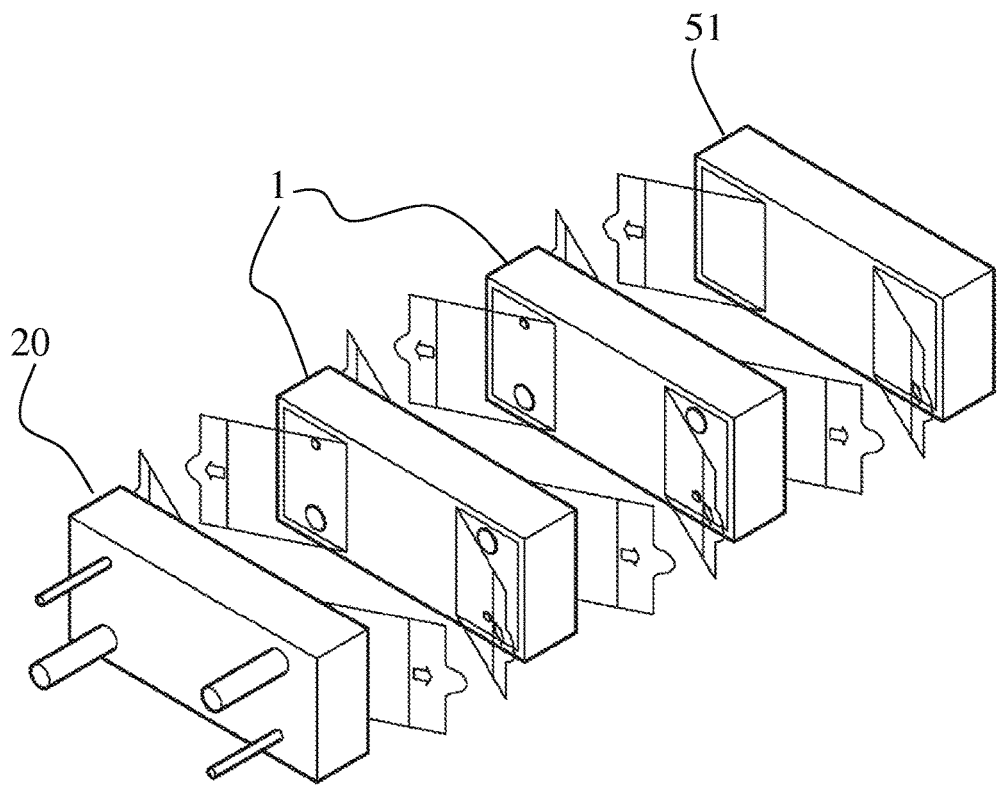
FIG. 4a shows a separation system according to one embodiment of the invention before the system is connected. The system comprises two separation units as shown in FIG. 1a, one fluid distribution unit as shown in FIGS. 2a and b and one end plate.

FIG. 4a shows a separation system according to one embodiment of the system before the system is connected. The system comprises two separation units 1 as shown in FIG. 1a, one fluid distribution unit 20 as shown in FIGS. 2a and 2b and one end plate 51. In this example the end plate 51 does not comprise any inlets or outlets. It is just a flat surface however provided with films to be mated with films on the closest separation unit 1. Here it can be seen how the films will be mated two and two together when the system is connected.

Figure 4B:
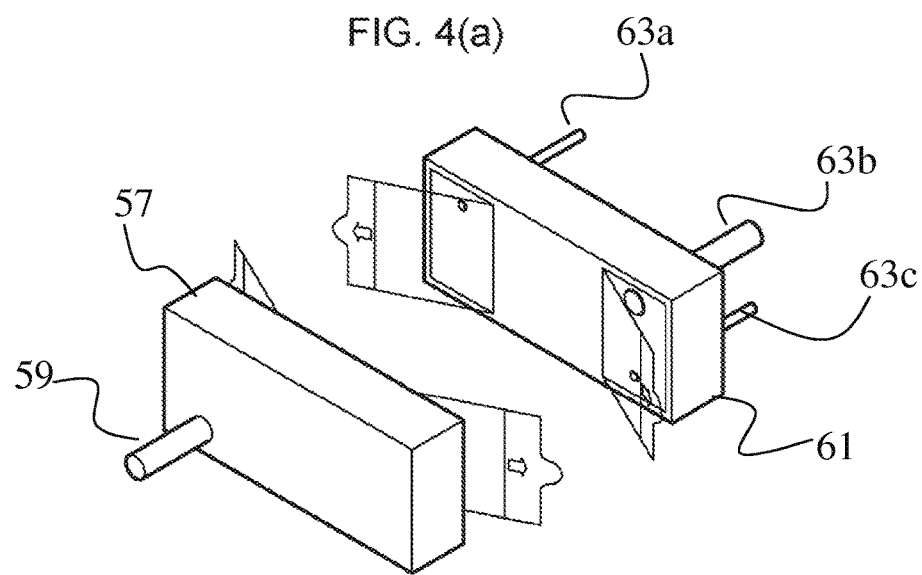
FIG. 4b shows another embodiment of fluid distribution units that can be used in a separation system as shown in FIG. 4a. Here two fluid distribution units are used where one provides only the feed inlet and the other provides permeate and retentate outlets.

FIG. 4b shows another embodiment of the separation system of FIG. 4a. In this embodiment a first fluid distribution unit 57 having only one inlet connection 59 and a second fluid distribution unit 61 having three outlet connections 63a, b, c are used instead of the fluid distribution unit 20 and the end plate 51 of FIG. 4a. This will give a different type of separation system but the inventive idea with aseptic connection by the use of the films is the same.

Other configurations of end plates and distribution plates are possible. For example, the filtrate outlet (permeate) may be collected by a single outlet connection instead of using two outlet connections as shown in FIGS. 4a and 4b. Equally, other positions or orientations of fluid connections, plates and cassettes are possible.

Figure 4C:
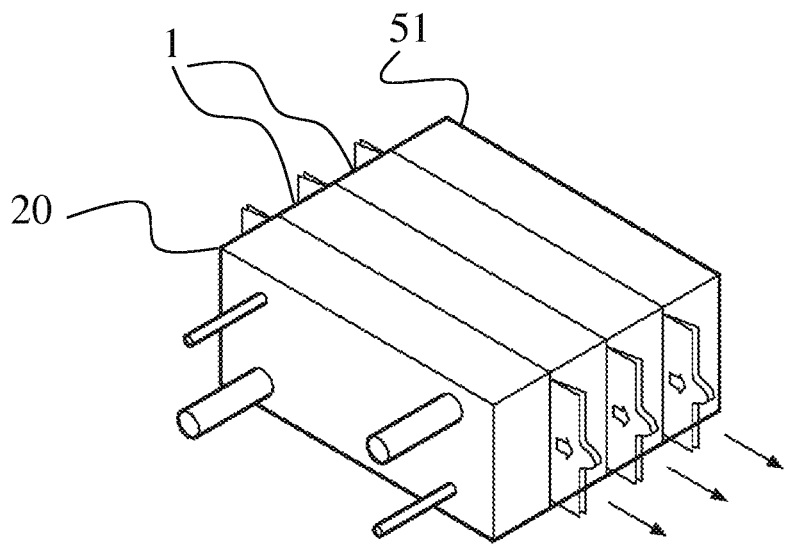
FIG. 4c shows the system of FIG. 4a in a first connection position where the films are released two and two together.

FIG. 4c shows the system of FIG. 4a in a first connection position where the films are released in the direction of the arrows two and two together. This first connection position has been achieved by bringing the surfaces to be connected to each other together and locking the system and its units in this first position. This can for example be achieved by means of a latching arrangement where mating locking parts are provided on each connecting side of the separation or reaction units and on the fluid distribution units. This could for example be protrusions with a hook on one side of the units and recesses adapted to receive the protrusions on the other side. When pressing the protrusions into the recesses the hooks need to pass over a shoulder which will latch the hook in place.

Another alternative for achieving the first connection position is to bring the system into a clamping device applying a moderate compression force on cassettes and end units. In this first connection position the parts of the films that are reaching outside the separation units 1 and the fluid distribution unit 20 and the end unit 51 are gripped two and two together and pulled out from the system.

Figure 4D:
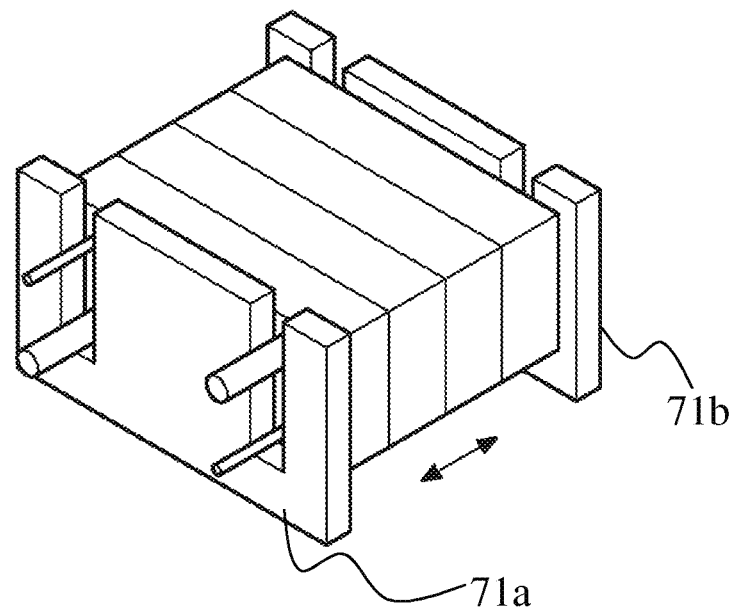
FIG. 4d shows the system of FIG. 4a in a second connection position (inserted into a clamp) where a fluid tight connection is provided.

FIG. 4d shows the system of FIG. 4a in a second connection position where a fluid tight connection is provided. This second connection position is achieved by applying more force to the fluid distribution unit 20 and the end unit 51 in the direction towards each other, i.e. the distance between all the parts of the system will be smaller and gaskets are engaged. In this example the separation system is provided inside a compression device comprising a first compression plate 71a and a second compression plate 71b to which a compressive force can be applied in order to achieve the fluid tight seal that is needed. The compression device 71a, 71b can be locked in the compressed position such that the fluid tight seal is maintained.

Figure 5A:
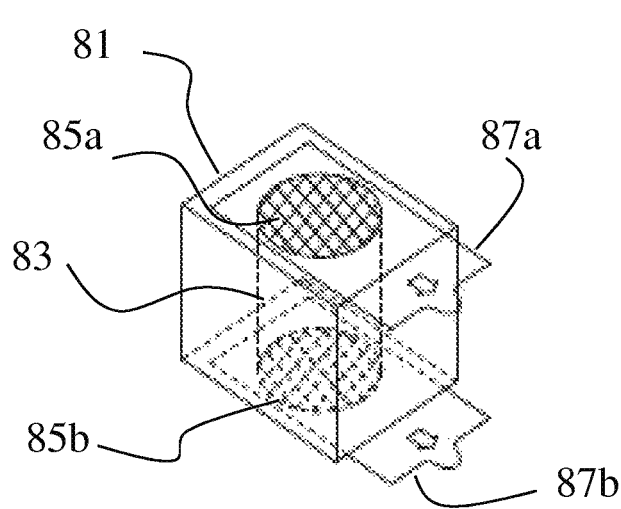
FIG. 5a shows a chromatography unit for connection in series according to one embodiment of the invention.

FIG. 5a shows a separation unit in the form of a chromatography unit 81 for connection in series according to one embodiment of the invention. In this embodiment the unit is provided as a cube. The chromatography unit 81 comprises a packed bed 83 with a filter 85a and 85b in each end of the packed bed 83 and facing the top and bottom of the unit respectively. These filters 85a, 85b will in this case be inlets/outlets of the unit. A protective film 87a and 87b of the same kind as described for previous embodiments of the invention is provided over each filter 85a, 85b. Hereby this chromatography unit can be connected to another chromatography unit of the same kind and the columns can be connected aseptically.

Figure 5B:
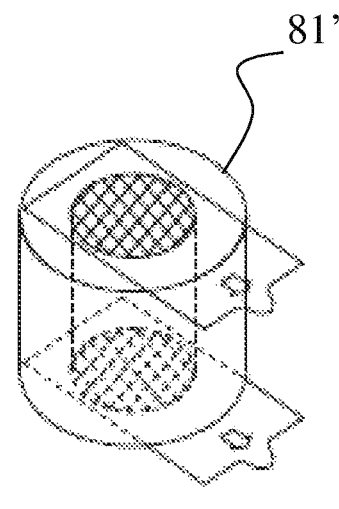
FIG. 5b shows a chromatography unit for connection in series according to another embodiment of the invention.

FIG. 5b shows a chromatography unit 81' for connection in series according to another embodiment of the invention. The only difference from the chromatography unit shown in FIG. 5a is that this unit is provided as a cylinder. Other geometries of the packed bed are possible. The packed bed may be made from particles and a suspension, respectively. Instead, the porous structure of the chromatography unit may also be provided as a block, for example as chemically prepared monolith or as a sintered structure. As described before, the packed bed and units may be configured as reaction unit, for example for conducting bioconversions.

Figure 5C:
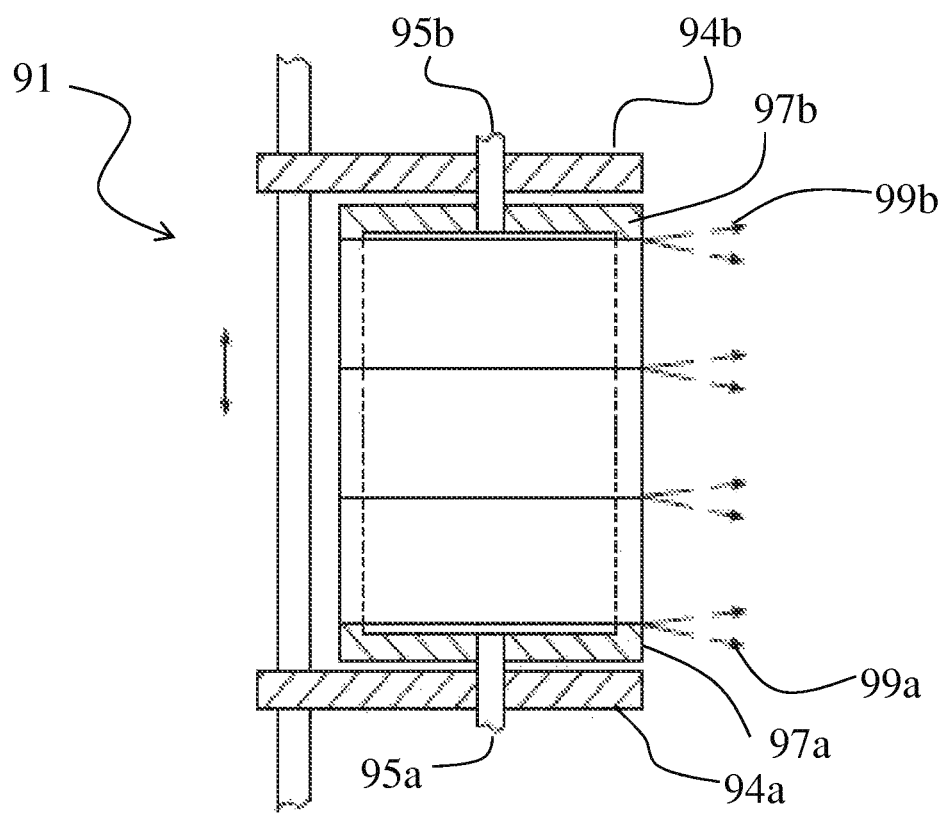
FIG. 5c shows a system where units as shown in FIG. 5a or b can be connected.

FIG. 5c shows a system 91 where units 81, 81' as shown in FIG. 5a or b can be connected. The system comprises a compression device 93 comprising a bottom compression plate 94a and an upper compression plate 94b between which a wanted number of chromatography units 81, 81' should be placed. The bottom compression plate 94a comprises a first inlet/outlet 95a and the upper compression plate comprises a second inlet/outlet 95*b*. The system 91 comprises further a first distribution plate 97*a* between the bottom compression plate 94*a* and the chromatography units to be positioned in the system. The first distribution plate 97*a* is further connected to the first inlet/outlet 95*a* and provided with a film 99*a* according to the invention. The film 99*a* is adapted to be mated with a film 87*b* of a chromatography unit 81, 81' that is positioned in the lowest position of the units that should be connected. The system 91 further comprises a second distribution plate 97*b* positioned between the upper compression plate 94*b* and the units to be placed into the system. The second distribution plate 97*b* is connected to the second inlet/outlet 95*b* and provided with a film 99*b* according to the invention.

In FIG. 5*c* it is shown how three chromatography units 81, 81' have been provided into the system 91. Also in this embodiment of the invention the units are compressed between the compression plates 94*a*, 94*b* to a first position where the mating films are released and then to a second position where a fluid tight seal is provided.

The chromatography units 81, 81' described above in relation to FIGS. 5*a*, 5*b* and 5*c* could also be provided as block materials, for example as a monoliths. In this case no filters are required. The films 87*a*, 87*b* are however provided in a similar way and a similar compression device 91 as the one described in relation to FIG. 5*c* can be used.

Figure 6A:
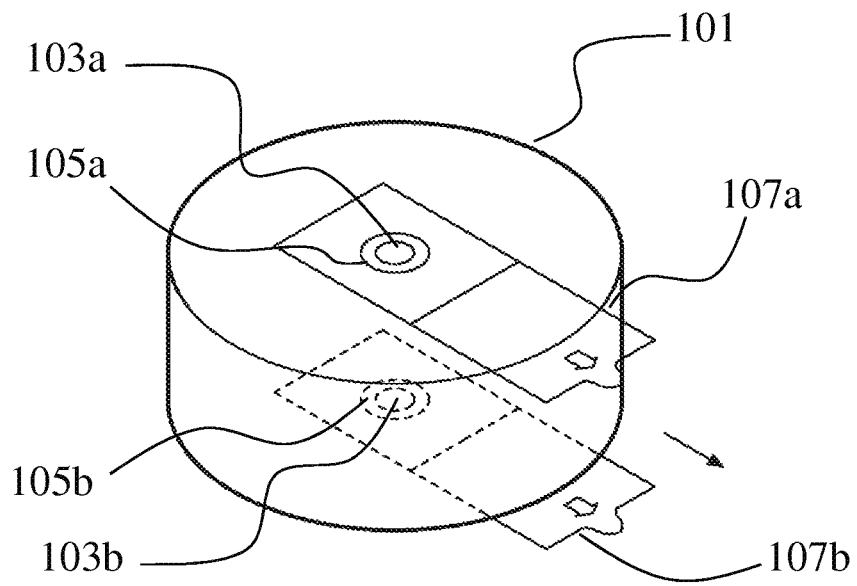
FIG. 6a shows another embodiment of a chromatography unit where the distribution/collection system is provided inside each unit.

FIG. 6*a* shows another embodiment of a separation unit in the form of a chromatography or reaction unit 101 where the distribution/collection system is provided inside each unit. Inside the chromatography or reaction unit 101 a distribution/collection system is provided in each end of a packed bed. This is not shown. A first inlet/outlet 103*a* is shown in the middle of one side of the chromatography or reaction unit 101 and a second inlet/outlet 103*b* is shown in the middle of the other side of the chromatography or reaction unit 101. Around the inlets/outlets 103*a*, 103*b* a gasket 105*a*, 105*b* and a foam layer (not shown) is provided as also shown in FIG. 3. A film 107*a*, 107*b* according to the invention is provided over each inlet/outlet 103*a*, 103*b*.

Figure 6B:
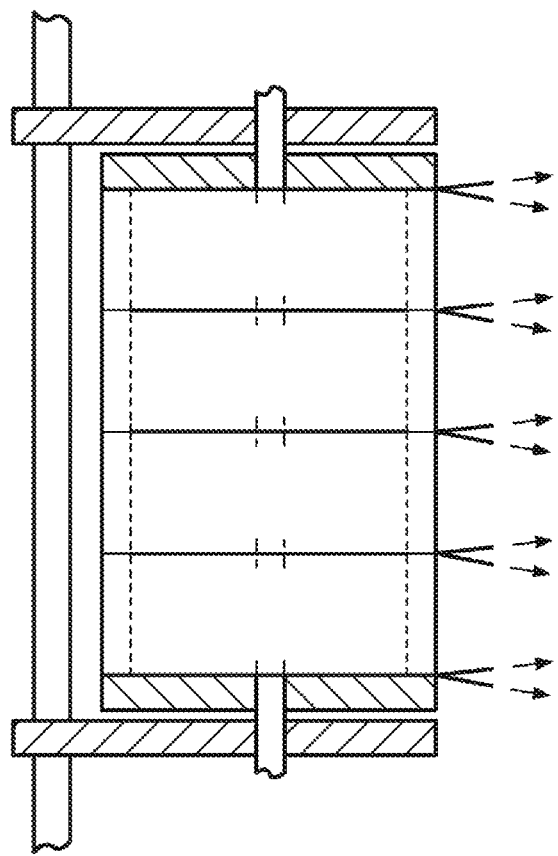
FIG. 6b shows a system where units as shown in FIG. 6a can be connected.

FIG. 6*b* shows a system where units as shown in FIG. 6*a* can be connected. The system is similar to the one shown in FIG. 5*c* and no further description is given here. The films are mated two and two as described above and an aseptic connection is provided between the units as described above.

In all these embodiments described above the parts and surfaces being in contact with a process fluid are suitably selected from materials that are in accordance with typical material requirements in (bio-)pharmaceutical manufacturing or food grade quality. For example, materials are suitably in compliance with USP Class VI and 21 CFR 177. Furthermore they are suitably of animal-free origin and compliance to EMEA/410/01.

The invention claimed is:

1. A method for providing aseptic connections between a first stackable unit and a second stackable unit to form a multi-unit device, the method comprising:
   providing on contact surfaces of the first stackable unit and the second stackable unit, plural fluid inlets/outlets comprising:
   at least two pairs of inlets/outlets on a first surface of the first stackable unit and at least two pairs of inlets/outlets on a second surface of the second stackable unit;
   providing a first film over a first pair of the inlets/outlets on the first stackable unit and a first film over a first pair of the inlets/outlets of the second stackable unit;
   providing a second film over a second pair of inlets/outlets on the first stackable unit and a second film over a second pair of inlets/outlets of the second stackable unit;
   connecting the first stackable unit with the second stackable unit;
   mating the first films of the first stackable unit and the second stackable unit together and mating the second films of the first stackable unit and the second stackable unit together, while the first stackable unit is in connection with the second stackable unit;
   forming an aseptic connection between the contact surface of the first stackable unit and the contact surface of the second stackable unit;
   providing a first compression plate and a second compression plate, wherein the first and second compression plate are configured to provide a compressive force;
   enabling a fluid tight connection between the first stackable unit and the second stable unit, wherein a first gasket is provided around the first pair of inlets/outlets of the first stackable unit and the second stackable unit, and a second gasket is provided around the second pair of inlets/outlets of the first stackable unit and the second stackable unit, and
   compressing, to a first position the mated first films and second films, wherein when the mated first films and the mated second films pulled out, compressing to a second position by applying a force by compression plates in a direction towards each other and engaging the first gaskets together and the second gaskets together thereby forming a fluid tight seal.

2. A stackable unit configured for combining with other stackable units to form a multi-unit device, the stackable unit comprising:
   on a contact surface thereof, providing plural fluid inlets/outlets comprising:
   a first pair of inlets/outlets on a first surface of the unit;
   a first film disposed overtop the first surface;
   a second pair of inlets/outlets on a second surface on a same contact surface of the stackable unit; and
   a second film disposed overtop the second surface;
   wherein a first stackable unit is configured to connect with a second stackable unit;
   wherein the first film of the stackable unit is configured to mate with a first film of another stackable unit, and the second film of the stackable unit is configured to be mated with a second film of the other stackable unit, while the stackable unit is in connection with the other stackable unit;
   wherein a first gasket is provided around the first pair of inlets/outlets of the stackable unit, and a second gasket is provided around the second pair of inlets/outlets of the stackable unit, wherein the first gasket mates a first gasket of the other stackable unit, and the second gasket mates with a second gasket of the other stackable unit while the stackable unit is in connection with the other stackable unit;
   wherein the first films and second films are configured to be removed concurrently while mating the first films and second films;
   wherein the stackable unit is configured to form an aseptic connection with the other stackable unit while removing of the first films and second films; and
   a compression device comprising a pair of compression plates, wherein the compression plates are configured to compress, to a first position the mated first films and second films, wherein when the mated first films and the mated second films are pulled out, compressing to a second position by applying a force by the compression plates in a direction towards each other and engaging the first gaskets together and the second gaskets together thereby forming a fluid tight seal.

3. The stackable unit of claim 2, further comprising a foam layer formed around each of the first gasket and the second gasket.

4. The stackable unit of claim 2, wherein at least one of the stackable unit and the other stackable unit includes a porous structure.

5. The stackable unit of claim 2, wherein the first film and the second film are unevenly folded over the first pair of inlets/outlets and the second pair of inlets/outlets, respectively.

6. The stackable unit of claim 2, wherein each compression plate fitted with a fluid port.

7. The stackable unit of claim 6, wherein a distribution plate is disposed between one of the the stackable unit and the other stackable unit, and the compression plate.

* * * * *